(12) United States Patent
Klemisch

(10) Patent No.: US 11,787,062 B2
(45) Date of Patent: Oct. 17, 2023

(54) EMOTIONAL INTELLIGENT ROBOTIC PILOT

(71) Applicant: The Boeing Company, Chicago, IL (US)

(72) Inventor: Jennifer Klemisch, Maple Valley, WA (US)

(73) Assignee: The Boeing Company, Chicago, IL (US)

( * ) Notice: Subject to any disclaimer, the term of this patent is extended or adjusted under 35 U.S.C. 154(b) by 896 days.

(21) Appl. No.: 16/711,773

(22) Filed: Dec. 12, 2019

(65) Prior Publication Data

US 2021/0178603 A1 Jun. 17, 2021

(51) Int. Cl.
| | |
|---|---|
| *G10L 25/63* | (2013.01) |
| *G06N 20/00* | (2019.01) |
| *G05D 1/00* | (2006.01) |
| *A61B 5/18* | (2006.01) |
| *G06F 40/56* | (2020.01) |
| *B25J 11/00* | (2006.01) |
| *G10L 25/66* | (2013.01) |
| *G05D 1/10* | (2006.01) |
| *A61B 5/00* | (2006.01) |

(52) U.S. Cl.
CPC .............. *B25J 11/001* (2013.01); *A61B 5/18* (2013.01); *A61B 5/6813* (2013.01); *B25J 11/0015* (2013.01); *G05D 1/0061* (2013.01); *G05D 1/0088* (2013.01); *G05D 1/101* (2013.01); *G06F 40/56* (2020.01); *G06N 20/00* (2019.01); *G10L 25/63* (2013.01); *G10L 25/66* (2013.01)

(58) Field of Classification Search
CPC ...... A61B 5/18; A61B 5/6813; B25J 11/0005; B25J 11/001; B25J 11/0015; B60W 50/10; G05D 1/0061; G05D 1/0088; G05D 1/101; G06F 40/30; G06F 40/56; G06F 40/58; G06N 3/02; G06N 3/10; G06N 20/00; G09B 9/08; G10L 17/26; G10L 25/48; G10L 25/63; G10L 25/66
USPC ......................................... 340/576
See application file for complete search history.

(56) References Cited

U.S. PATENT DOCUMENTS

| | | | | |
|---|---|---|---|---|
| 2015/0338917 | A1* | 11/2015 | Steiner | H04L 9/3271 345/156 |
| 2018/0136615 | A1* | 5/2018 | Kim | B25J 11/001 |
| 2019/0050774 | A1* | 2/2019 | Divine | G16H 50/20 |
| 2020/0130705 | A1* | 4/2020 | Boss | B60W 50/085 |
| 2020/0310939 | A1* | 10/2020 | Kußmaul | G06N 3/084 |
| 2020/0401934 | A1* | 12/2020 | Trim | G16H 40/67 |
| 2021/0056167 | A1* | 2/2021 | Lam | G06Q 50/01 |
| 2021/0107504 | A1* | 4/2021 | Shtrom | A61B 5/0507 |

(Continued)

*Primary Examiner* — Stephen R Burgdorf
(74) *Attorney, Agent, or Firm* — PARSONS BEHLE & LATIMER

(57) ABSTRACT

A system for providing pilot or controller support in a reduced crew transport environment may include a set of sensors configured to collect a set of measurements of a set of physiological signals of a user. The system may further include an emotional analyzer model usable to generate at least one emotional parameter value corresponding to the set of measurements. The system may also include a natural language processing model usable to generate a natural language statement corresponding to the at least one emotional parameter value for output to the pilot.

20 Claims, 6 Drawing Sheets

(56) References Cited

U.S. PATENT DOCUMENTS

2021/0394762 A1* 12/2021 Neveu .................... A61B 5/165
2022/0284737 A1* 9/2022 Schwindt ................ G10L 25/63

* cited by examiner

EMOTIONAL INTELLIGENT ROBOTIC PILOT

FIELD OF THE DISCLOSURE

This disclosure is generally related to the field of robotic and automatic pilot systems and, in particular, to an emotional intelligent robotic pilot.

BACKGROUND

Human interactions are an integral part of any team performance. The dynamics in a team with an imbalance of power may reduce the overall efficiency and performance of the team. A balanced crew resource management (CRM) policy in a vehicle or control room environment seeks to have each user's (e.g., pilot's) contributions equally weighted and valued. Successful CRM policies may result in a significant reduction of incidents. Effective CRM is dependent on crew coordination and human interactions, of which emotional awareness may be a critical component.

In some cases, a user may find themselves in a reduced crew environment. A reduced crew environment is one in which a user is placed in a piloting or control environment that typically includes more pilots or controllers than are present. Robotic assistance may be used to compensate for having fewer users. For example, in some cases, an aircraft may typically have two pilots, but may become a reduced crew environment when flown by a single pilot along with a robotic piloting system.

Reduced crew environments may increase the possibility of unbalanced CRM. For example, existing robotic pilots may have relevant information and equipment control but may lack the ability to communicate effectively with people. In such systems, robotic pilots may perform knob turning, button pushing, and column maneuvering aspects of flying. However, these systems may lack the critical component of having an equal partner and providing balanced CRM because they are unable to connect with a human at an emotional level.

SUMMARY

Described is an emotionally intelligent robotic pilot that measures physiological signals associated with a user and generates an appropriate natural language statement corresponding to an emotion of the user. In an example, a system for providing user support in a robotic-assisted user environment includes at least one processor and memory storing instructions that, when executed by the at least one processor, cause the at least one processor to receive a set of measurements of a set of physiological signals from a set of sensors applied to a user. The processor further generates at least one emotional parameter value corresponding to the set of measurements based on an emotional analyzer model. The processor also generates a natural language statement corresponding to the at least one emotional parameter value based on a natural language processing model.

In some examples the set of sensors includes one or more microphones, one or more biometric sensors, one or more cameras, or any combination thereof. In some examples, the set of physiological signals includes a galvanic skin response, a blood volume measurement, a heart rate variability, an electroencephalogram, an eye dilation measurement, a thermal response, a muscle response, or any combination thereof. In some examples, the instructions further cause the at least one processor to convert the set of measurements into a format that is compatible with the emotional analyzer model.

In some examples, the instructions further cause the at least one processor to receive user calibration data associated with the user, where the at least one emotional parameter value is generated based at least in part on the user calibration data, and where the natural language statement is generated based at least in part on the user calibration data. In some examples, the user calibration data includes a value representing a level of emotional response associated with a user, a user communication preference value, or both. In some examples, the system includes a user corpus stored in a database, the user corpus including the user calibration data associated with the user along with additional user calibration data associated with additional users, where the user calibration data is retrieved from the user corpus.

In some examples, the instructions further cause the at least one processor to receive environmental data, wherein the at least one emotional parameter value is generated based at least in part on the environmental data. In some examples, the environmental data indicates a temperature, a pressure, weather conditions, visual conditions, or any combination thereof. In some examples, the instructions further cause the at least one processor to receive vehicle activity data, where the emotional parameter value is generated based at least in part on the vehicle activity data, and where the natural language statement is generated based at least in part on the vehicle activity data. In some examples, the vehicle activity data indicates a state of an aircraft, a phase of flight associated with the aircraft, activated warnings associated with the aircraft, air traffic control communications, aircraft imaging or radar inputs or any combination thereof.

In some examples, the emotional parameter value includes a valence parameter, an arousal parameter, a dominance parameter, an emotion parameter, a strength parameter, or any combination thereof. In some examples, the system includes an affect training database storing training data that maps sample physiological signals to emotional parameter values, where the emotional analyzer model is a machine learning model trained using the training data. In some examples, the instructions further cause the at least one processor to output the natural language statement to the user, receive a user response to the natural language statement, and initiate an update to an affect training database, a user corpus database, or both based on the user response. In some examples, the system is implemented within a robotic-assisted transport vehicle or a vehicle control station.

In an example, a method for providing user support in a robotic-assisted user environment includes receiving a set of measurements of a set of physiological signals from a set of sensors applied to a user. The method further includes generating at least one emotional parameter value corresponding to the set of measurements based on an emotional analyzer model, based on user calibration data retrieved from a user corpus stored at a database, and based on environmental data, where the emotional analyzer model is trained based on an affect training database. The method also includes generating a natural language statement corresponding to the at least one emotional parameter value based on a natural language processing model. The method includes outputting the natural language statement to the user. The method further includes receiving a user response to the natural language statement. The method also includes updating the affect training database, the user corpus, or both based on the user response.

In some examples, the method includes receiving training data that maps sample physiological signals to emotional parameter values from the affect training database and training the emotional analyzer model using the training data. In some examples, outputting the natural language statement to the user includes generating a visible signal, and audio signal, or a combination thereof.

In an example, a system for providing pilot or controller support in a reduced crew transport environment includes a set of sensors configured to collect a set of measurements of a set of physiological signals of a pilot. The system further includes an emotional analyzer model usable to generate at least one emotional parameter value corresponding to the set of measurements. The system also includes a natural language processing model usable to generate a natural language statement corresponding to the at least one emotional parameter value for output to the pilot.

In some examples, the system includes one or more aircraft systems to provide environmental data and aircraft activity data for use in generating the at least one emotional parameter value, an affect training database to provide training data for training the emotional analyzer model, and a user corpus stored in a database, the user corpus including the user calibration data associated with the pilot to provide pilot-specific data for use in generating the at least one emotional parameter value and for use in generating the natural language statement.

Figure 1:
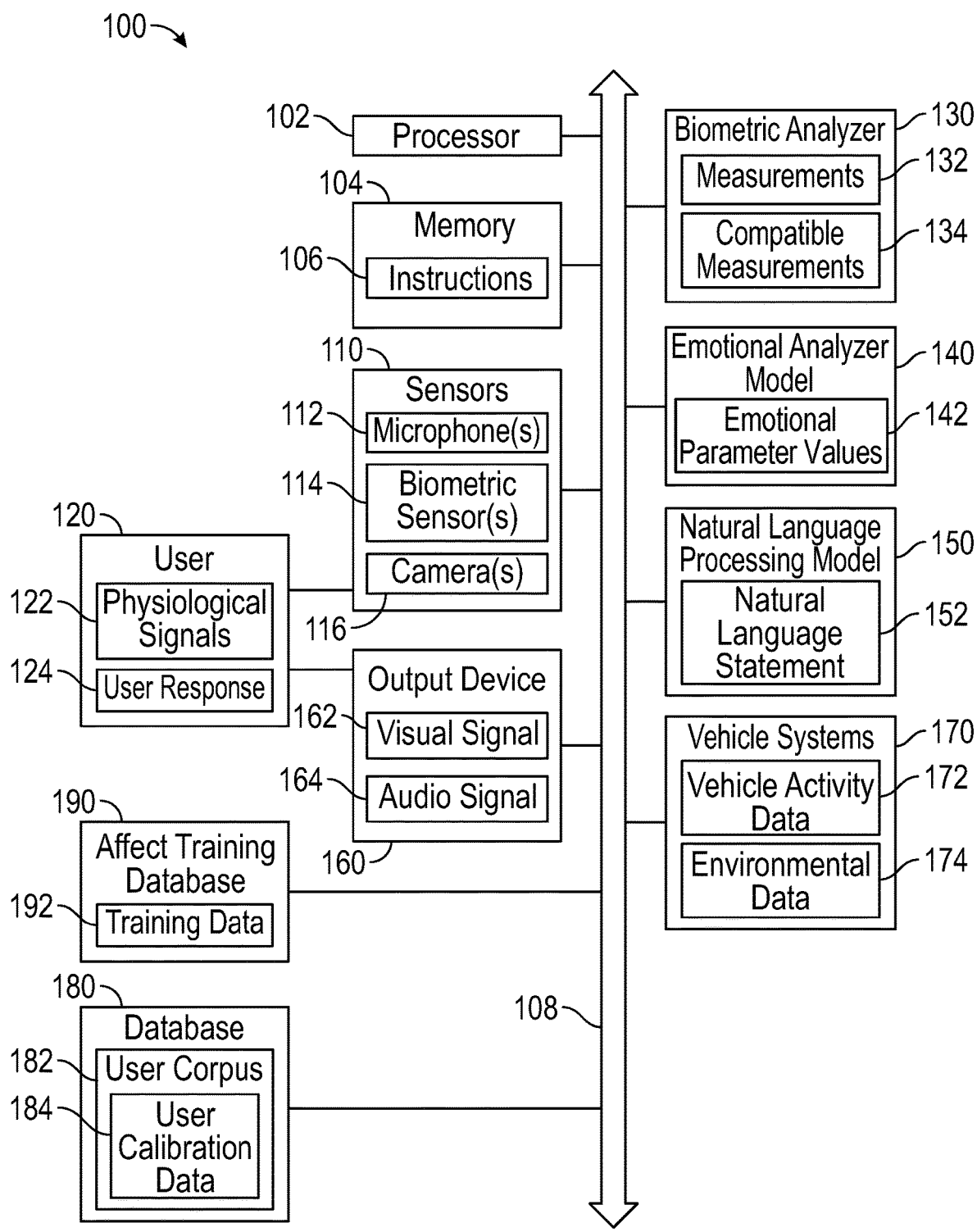
FIG. 1 is a block diagram depicting an example of a system for providing user support in a robotic-assisted user environment.

While the disclosure is susceptible to various modifications and alternative forms, specific examples have been shown by way of example in the drawings and will be described in detail herein. However, it should be understood that the disclosure is not intended to be limited to the particular forms disclosed. Rather, the intention is to cover all modifications, equivalents and alternatives falling within the scope of the disclosure.

DETAILED DESCRIPTION

A robotic assisted piloted aircraft, another type of vehicle, or a control room may be more productive when a robotic counterpart has the capability, not only turn knobs and push buttons, but to respond to a user in an emotionally intelligent manner, both in actions and communications. The disclosed system and method may enable a robotic pilot to act like a human co-pilot responding with increased awareness and commentary, and with increased workload.

Referring to FIG. 1, a system 100 for providing user support in a robotic-assisted user environment is depicted. The system 100 may include at least one processor 102 and memory 104. The processor 102 may include a central processing unit (CPU), a graphical processing unit (GPU), a digital signal processor (DSP), a peripheral interface controller (PIC), or another type of microprocessor. It may be implemented as an integrated circuit, a field programmable gate array (FPGA), an application specific integrated circuit (ASIC), a combination of logic gate circuitry, other types of digital or analog electrical design components, or the like, or combinations thereof. In some examples, the processor 102 may be distributed across multiple processing elements, relying on distributive processing operations.

The memory 104 may include random-access memory (RAM), read-only memory (ROM), magnetic disk memory, optical disk memory, flash memory, another type of memory capable of storing data and processor instructions, or the like, or combinations thereof. In some examples, the memory 104, or portions thereof, may be located externally or remotely from the rest of the system 100. The memory 104 may store instructions 106 that, when executed by the processor 102, cause the processor 102 to perform operations. The operations may correspond to any operations described herein as being performed by the system 100.

The system 100 may include a set of sensors 110, a biometric analyzer 130, an emotional analyzer model 140, a natural language processing model 150, and an output device 160. These devices may be implemented as part of the instructions 106 and their functions may be performed by the at least one processor 102. Alternatively, they may be implemented as discrete circuit modules. In some cases, one or more modules may be combined. The system 100 may further include vehicle systems 170, an affect training database 190, and a database 180 including a user corpus 182. These may be part of the system 100, as depicted in FIG. 1. Alternatively, some or all of them may be distinct and/or remotely located from the system 100. FIG. 1 depicts a bus 108 connecting each of the systems, modules, and databases. In practice, multiple buses, networks, and/or the internet may be used to communicatively connect the modules depicted in FIG. 1.

The set of sensors 110 may be configured to measure a set of physiological signals 122 associated with the user 120. The user 120 may be a pilot. The set of sensors 110 may include one or more microphones 112, one or more biometric sensors 114, one or more cameras 116, another type of wearable or user specific sensor, or any combination thereof. The set of physiological signals 122 may include a galvanic skin response, a blood volume measurement, a heart rate variability, an electroencephalogram, an eye dilation measurement, a thermal response, a muscle response, another type of physiological measurement related to user stress or emotion, or any combination thereof.

The biometric analyzer 130 may be configured to convert a set of measurements 132 of the set of physiological signals 122 to compatible measurements 134 that are usable with the emotional analyzer model 140. The conversion may include analog-to-digital conversions, file format conversions, digital preprocessing processes, data extraction processes, and/or other types of conversion processes. As a non-limiting illustrative example, the conversions may include processes such as analyzing video or photographic footage of the user's 120 face to generate a measurement corresponding to a facial state value. Another example may include converting raw heart rate data into a time varying frequency pattern. Many other examples are possible.

The emotional analyzer model 140 may be usable to generate at least one emotional parameter value 142 corresponding to the set of measurements 132. The emotional analyzer model 140 may include an artificial intelligence and/or machine learning model usable to identify and/or quantify the at least one emotional parameter value 142. For example, the emotional analyzer model 140 may use various algorithms to process the biometric signal data into one or more emotional parameters, some examples include Ant colony optimization, genetic algorithms, evolutionary algorithms, learning classifier systems, self-organizing maps, other types of machine learning classification techniques, or an ensemble model. It may be implemented as a neural network, decision trees, nonlinear regression, logistic regression, other types of machine learning classification models, or combinations thereof.

The emotional parameter 142 may include a valence parameter, an arousal parameter, a dominance parameter, an emotion parameter, a strength parameter, or any combination thereof. Together, these parameters may be usable to analyze emotions associated with the user 120. For example, a positive valence with low emotional parameters may indicate that the user 120 is relaxed and may be more open to conversation with the system 100, while a negative valence with high emotional parameters may indicate that the user 120 is in a tense situation and quick, succinct communication is preferable.

The natural language processing model 150 may be usable to generate a natural language statement 152 corresponding to the at least one emotional parameter value 142. The natural language processing model 150 may likewise include content determination, discourse planning, sentence aggregation, lexicalization, referring expression generation, and linguistic realization. Any of these phases may use one or more algorithms for generating the content. Common algorithms for generating referring expressions include greedy algorithms, Incremental algorithms, Boolean expressions, Context-Sensitive extensions and Sets algorithms, among others, or combinations thereof.

The natural language statement 152 may complement the one or more emotional parameter 142. For example, if the emotional parameter indicates a relaxed situation, then the natural language statement may include a relaxed and familiar tone (e.g., "I can help you with a few tasks if you'd like"). In contrast, if the emotional parameter indicates a tense situation, then the natural language statement may include a more direct tone to address the situation (e.g., "The engine warning is on, I'm starting engine warning procedures").

The output device 160 may include any device capable of communicating the natural language statement 152 to the user 120. The natural language statement 152 may be communicated through a visual signal 162, an audio signal 164, or both. Examples of the output device 160 may include a visual display screen, a speaker system, another type of audio/visual device, or any combination thereof.

The vehicle systems 170 may include systems usable to operate a vehicle, such as an aircraft, and may be associated with vehicle activity data 172. For example, the vehicle activity data 172 may indicate a state of the vehicle, such a phase of flight, activated warnings, air traffic control communications, aircraft imaging or radar inputs, other types of system states and/or data, or any combination thereof. The emotional parameter value 142 may be generated based at least in part on the vehicle activity data 172. Likewise, the natural language statement 152 may be generated based at least in part on the vehicle activity data 172. As an illustrative example, during a takeoff and/or landing phase, the emotional parameter value 142 may be more indicative of stress and the natural language statement 152 may be less conversational and more concise as compared to other phases of flight. Other examples exist.

The vehicle system 170 may further be configured to measure, or otherwise detect, environmental data 174. The environmental data 174 may indicate a temperature, a pressure, weather conditions, visual conditions, other indications of environmental conditions, or any combination thereof. The at least one emotional parameter value 142 may be generated based at least in part on the environmental data 174.

The user corpus 182 stored in the database 180 may include user collaboration data associated with a plurality of users that may use the system 100. For example, the user corpus 182 may include user calibration data 184 associated with the user 120 along with additional user calibration data associated with additional users. The user calibration data 184 may include a value representing a level of emotional response associated with the user 120, a user communication preference value, or both. The at least one emotional parameter value 142 may be generated based at least in part on the user calibration data 184, and the natural language statement 152 may be generated based at least in part on the user calibration data 184. To illustrate, the emotional parameter value 142 may be more indicative of a calm emotion when the user calibration data indicates that the user 120 is less prone to emotional responses. Other examples exist.

The affect training database 190 may store training data 192 that maps sample physiological signals to emotional parameter values. The emotional analyzer model 140 may be a machine learning model trained using the training data 192. Training the emotional analyzer model 140 may be an ongoing process. For example, a user response 124 may be received from the user 120 in response to the natural language statement 152. The affect training database 190 may be updated based on the user response 124 and the emotional analyzer model 140 may be further trained or otherwise updated. The user corpus 182 may also be updated based on the user response 124.

During operation the processor 102 may detect an event or situation for which the system 100 may assist the user 120. For example, a particular phase of flight may be detected, or a situation typically associated with stress, or some level of stress with respect to the user 120 may be detected. Physiological signals 122 associated with the user 120 may be measured and stored as the measurements 132. In order to use the emotional analyzer model 140, the measurements may be converted or otherwise altered for compatibility to generate the compatible measurements 134. The emotional analyzer model 140 may classify and quantify various properties of the physiological signals 122 in order to determine one or more emotional parameters 142 associated with the user 120. Based at least partially on the emotional parameters 142, the system 100 may use the natural language processing model 150 to generate a natural language statement 152 that is appropriate based on the physiological signals 122 and output the natural language statement 152 to the user 120 via the output device 160. The system 100 may also take appropriate action by controlling one or more of the vehicle systems 170.

Further during operation, the system 100 may use the user calibration data 184 to tune the emotional analyzer model 140. For example, a level of emotion may be different for different users. The user calibration data 184 can be used to apply different weights or importance to the measurements 132 based on which user is interacting with the system 100. By weighting the measurements 132, the emotional parameters 142 may be more accurate with respect to a specific user. Further, the user 120 may have a preference in language used to address the user 120. That preference may be stored in the user calibration data 184 and used by the natural language processing model 150 to ensure the natural language statement 152 is appropriate for the user 120.

The system 100 may also use the vehicle activity data 172 and the environmental data 174 in generating the emotional parameters 142 and the natural language statement 152. To illustrate, in a situation where the emotional parameters 142 indicate high levels of stress in the user 120, the natural language statement 152 may note that the user 120 seems agitated. However, if the vehicle activity data 172 indicates that a phase of flight is in takeoff or landing, then it is less likely that the stress is due to agitation because the takeoff and landing phases are inherently higher stress activities.

The user 120 may respond to the natural language statement 152, or to actions taken by the system 100. These user responses 124 may be used to add to the training data 192 for further training of the emotional analyzer model 140. In this way, the system 100 may continuously improve its accuracy in sensing emotions associated with the user 120 and generating the appropriate natural language statement 152 as a response.

A benefit of the system 100 is that a good CRM balance may be achieved between the user 120 and a robotic co-pilot to ensure safety and reliability of flying. The system 100 may provide sufficient emotional sensing and feedback to enable a robotic pilot to fully contribute to the piloting task. Other benefits may exist.

Figure 2:
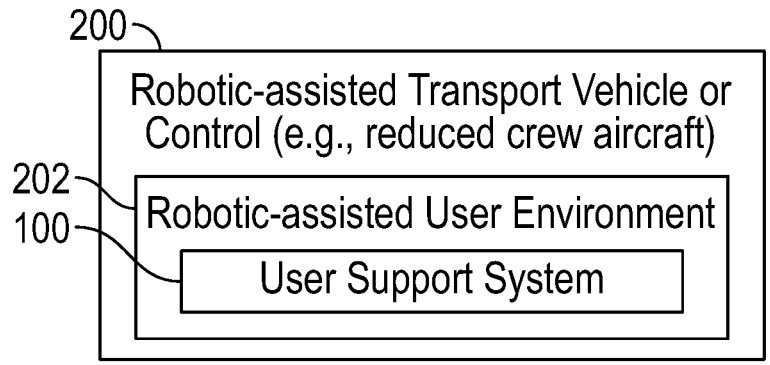
FIG. 2 is a block diagram depicting an example of a robotic-assisted transport vehicle or control.

Referring to FIG. 2, an example of a robotic-assisted transport vehicle or control system 200 is depicted. For example, the vehicle or control system 200 may include an aircraft, watercraft, spacecraft, an air traffic control system, or another type of piloted vehicle or control system. The vehicle or control system 200 may include a robotic-assisted user environment 202. The robotic assistance may compensate for the vehicle or control system 200 having fewer crew members than a typical vehicle or control system. The system 100 may be incorporated into the robotic-assisted user environment 202. By incorporating the system 100 into the robotic-assisted user environment 202, a good CRM balance may be maintained within the robotic-assisted transport vehicle or control system 200 without performance loss in the case of a reduced crew.

Figure 3:
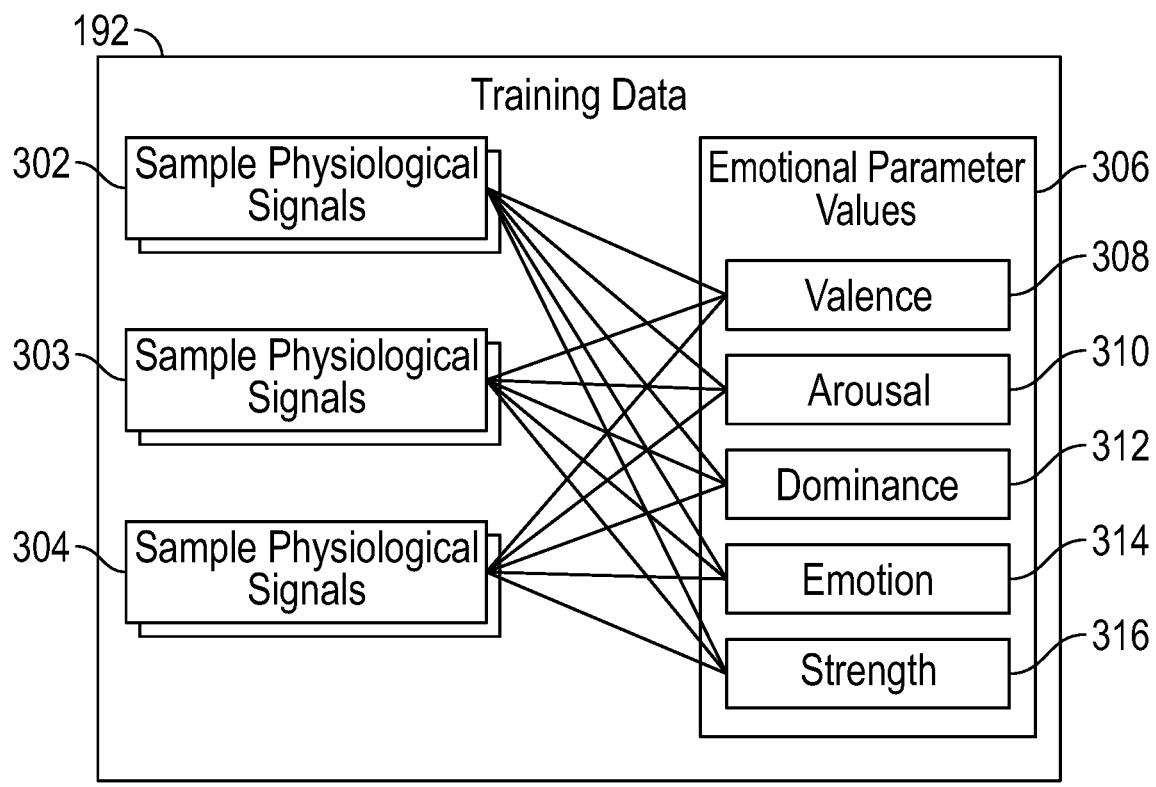
FIG. 3 is a diagram depicting example training data for use with training an emotional analyzer model.

Referring to FIG. 3, an example of training data 192 for use with the affect database 190 is depicted. As shown in FIG. 3, the training data 192 may map sample physiological signals 302, 303, 304, to emotional parameter values 306. The emotional parameter values 306 may combine to describe a particular affect. For example, the emotional parameter values 306 may include describe a valence 308, an arousal 310, a dominance 312, an emotion 314, and/or a strength 316. In some cases, the dominance 312, the valence 308, and the arousal 310 may be used individually or to identify the emotion 314. The training data may be used to train the emotional analyzer model 140. By using a sufficient amount of training data 192 and machine learning techniques, the emotional analyzer model 140 may learn how the sample physiological signals 302, 303, 304, apply to particular levels of each of the emotional parameters 306. Thus, the emotional analyzer model 140 may develop the ability to detect particular nuances in various combinations of the sample physiological signals 302, 303, 304. In some cases, training data, such as the training data 192, may enable predictive models to be generated that are more complete and accurate than predictions made based on human observations.

Figure 4:
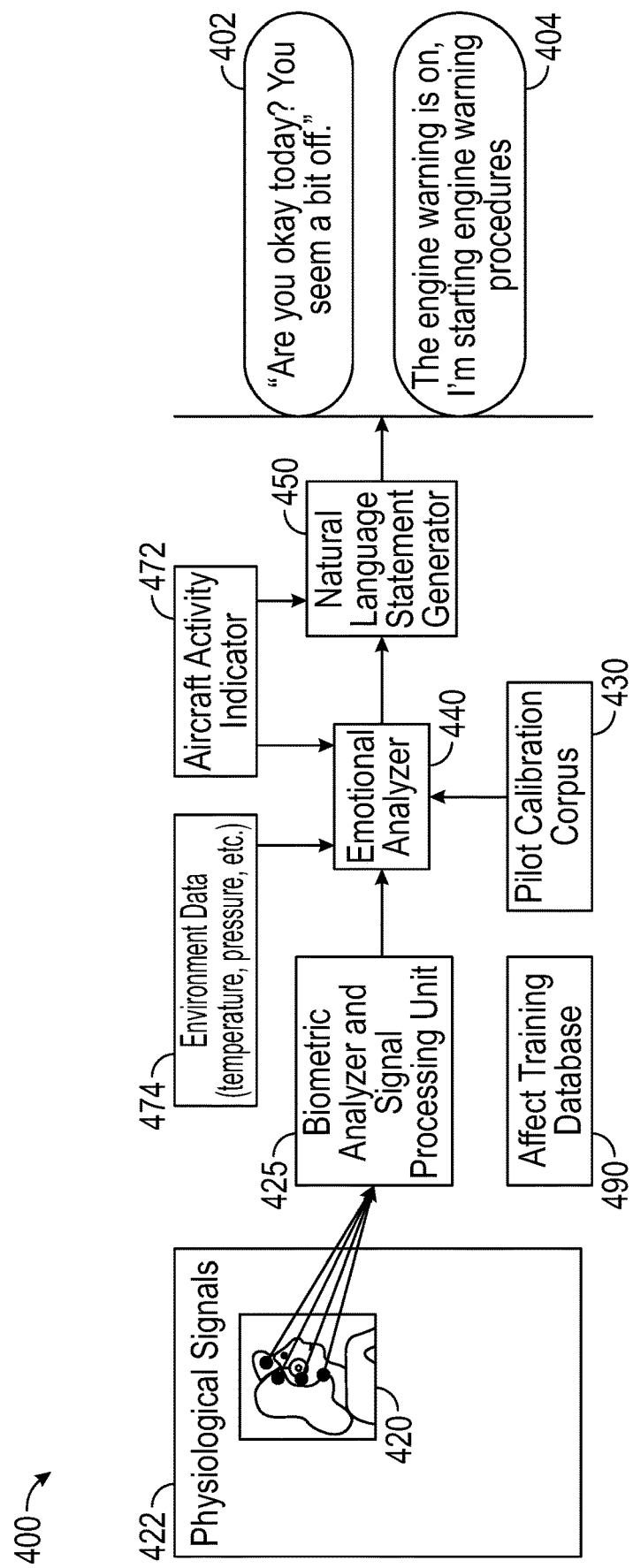
FIG. 4 is a conceptual diagram depicting an example of a process for providing user support in a robotic-assisted user environment.

Referring to FIG. 4 a conceptual diagram of an example of a process 400 for providing user support in a robotic-assisted user environment is depicted. The process 400 may apply in the particular case of an aircraft. However, it should be noted that other applications exist. The process 400 may include measuring a set of physiological signals 422 associated with a user 420. The physiological signals may correspond to the set of physiological signals 122 of FIG. 1. Then, a biometric analyzer and signal processing unit 425 may clean and analyze the physiological signals 422 and aggregate data. An emotional analyzer 440 may use machine learning algorithms and constructs (e.g., the emotional analyzer model 140 of FIG. 1) to perform feature extraction and classification of emotion. A pilot calibration corpus 430 may be used to tailor emotional sensing and responses for individual pilots.

Environmental data 474, such as a temperature or pressure, may be used to calibrate the biometric signals and influence the extraction and classification of the emotion from the emotional analyzer 440. Aircraft activity indicator data 472 may include information such as a phase of flight and aircraft activity level, which can be used in determining the emotion at the emotional analyzer 440. For example, a high heart rate may be expected during landing in icy conditions, and communication with the user 420 may be brief and limited to critical information. A natural language statement generator 450 may generate appropriate communications based on the output of the emotional analyzer 440. The natural language statement generator 450 may also rely on the aircraft activity indicator data 472 in generating outputs to the user 420. An affect training database 490 may store training data to continuously improve the machine learning model associated with the emotional analyzer 440.

As a sample output of the process 400, the natural language statement generator 450 may generate a first comment 402 such as "Are you okay today? You seem a bit off," or a second comment 404, such as "The engine warning is on, I'm starting engine warning procedures." Different comments may be generated based on the different situations and emotions detected by the emotional analyzer 440.

Each of the components depicted in FIG. 4 may include separate circuitry to perform their associated functions. Alternatively, each of the components depicted in FIG. 4 may be performed by one or more computing devices, such as a processor. Further, any of the components of FIG. 4 may be combined with any other of the components.

Figure 5:
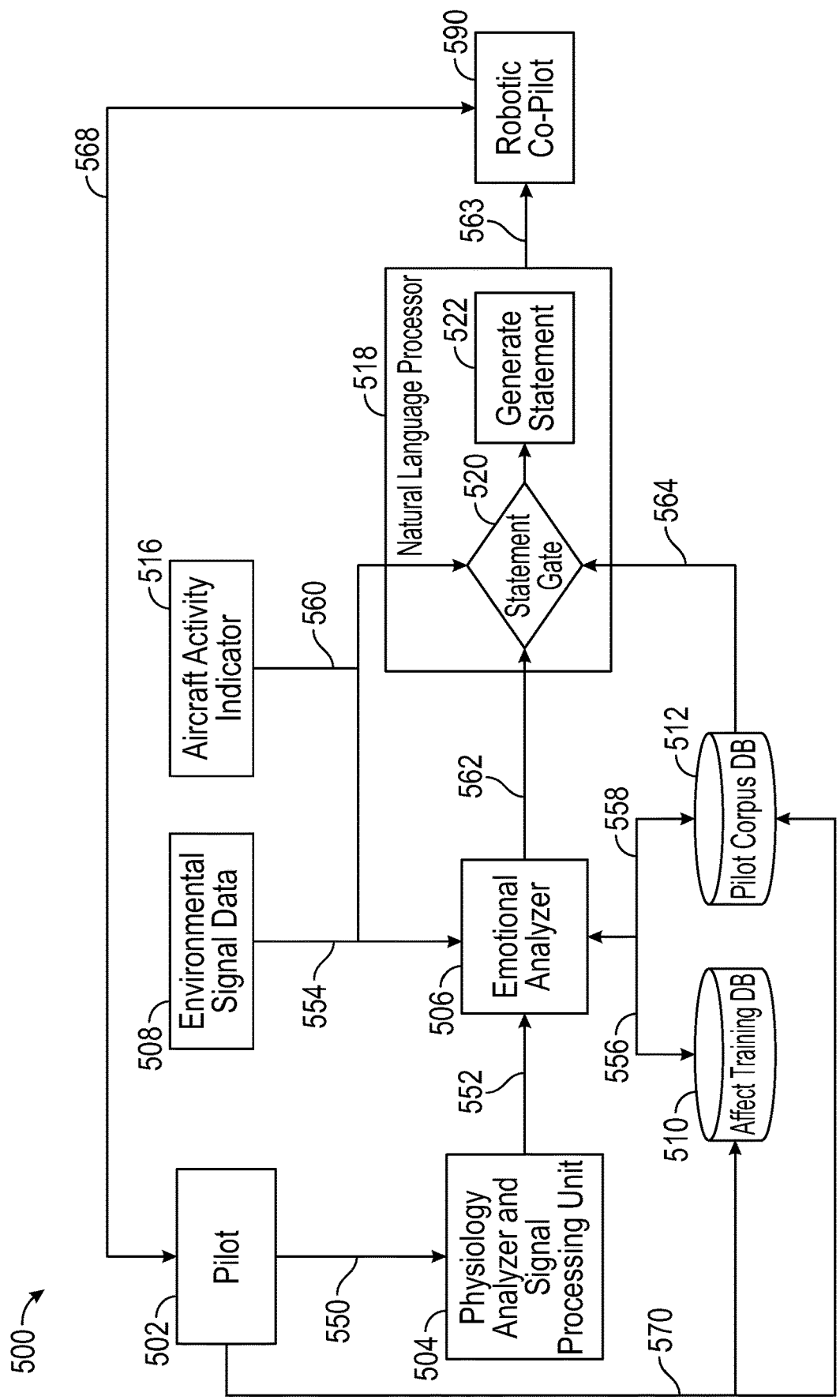
FIG. 5 is a flow diagram depicting an example of a method for providing user support in a robotic-assisted user environment.

Referring to FIG. 5, a dataflow diagram depicting an example of a dataflow 500 for providing user support in a robotic-assisted user environment is depicted. The dataflow 500 may begin with a pilot 502. As with FIG. 4, although FIG. 5 is described with reference to an aircraft, other applications are possible.

Raw physiological signal data 550 may be measured from the pilot 502 and passed to a physiology analyzer and signal processing unit 504. Processed, aggregated, and cleaned data 552 may pass from the physiology analyzer and signal processing unit 504 to an emotional analyzer 506. The emotional analyzer 506 may receive temperature, pressure, weather, and/or visual imagery data 554 from environmental signal data 508. The emotional analyzer 506 may include a machine learning model that was trained using affect computing training data 556 received from an affect training database 510. The emotional analyzer 506 may receive pilot emotional calibration and prior response data 558 from a pilot corpus database 512. The emotional analyzer 506 may also receive aircraft situational awareness data 560, including but not limited to, phase of flight data, system failures data, aircraft warnings data, and aircraft traffic control communication data, from an aircraft activity indictor 516. Based on the received data, the emotional analyzer 506 may generate predicted affect, valence, arousal, emotion, and strength data 562, which may be passed to a natural language processor 518.

The natural language processor 518 may include a statement gate 520 that can be used in determining an emotionally appropriate response. For example, the statement gate 520 may determine whether to make a statement or not to make a statement, and whether the statement is relatively brief or long. The determination may be made based on pilot communication preferences 564 received from the pilot corpus database 512, based on the aircraft situational awareness data 560, and based on the predicted affect, valence, arousal, emotion, and strength data 562. When the statement gate 520 determines that a statement should be generated, a generate statement module 522 may be used to generate an affect influenced action statement 563, which may be passed to a robotic co-pilot 590. The statement 563 may indicate that a particular action is being taken by the robotic co-pilot 590.

The robotic co-pilot 590 may send the statement 568 to the pilot 502 and may receive a response from the pilot 502. For example, the pilot 502 may instruct to robotic co-pilot 590 to refrain from taking the suggested action. A pilot response 570 may also be used to update the affect training database 510 and the pilot corpus database 512.

The dataflow 500 may enable a system, such as the system 100 of FIG. 1, to sense an emotion of the pilot 502 and generate an appropriate emotional response. The system may also be continuously updated to ensure that the robotic co-pilot takes actions and makes statements that are appropriate to the pilot 502.

Figure 6:
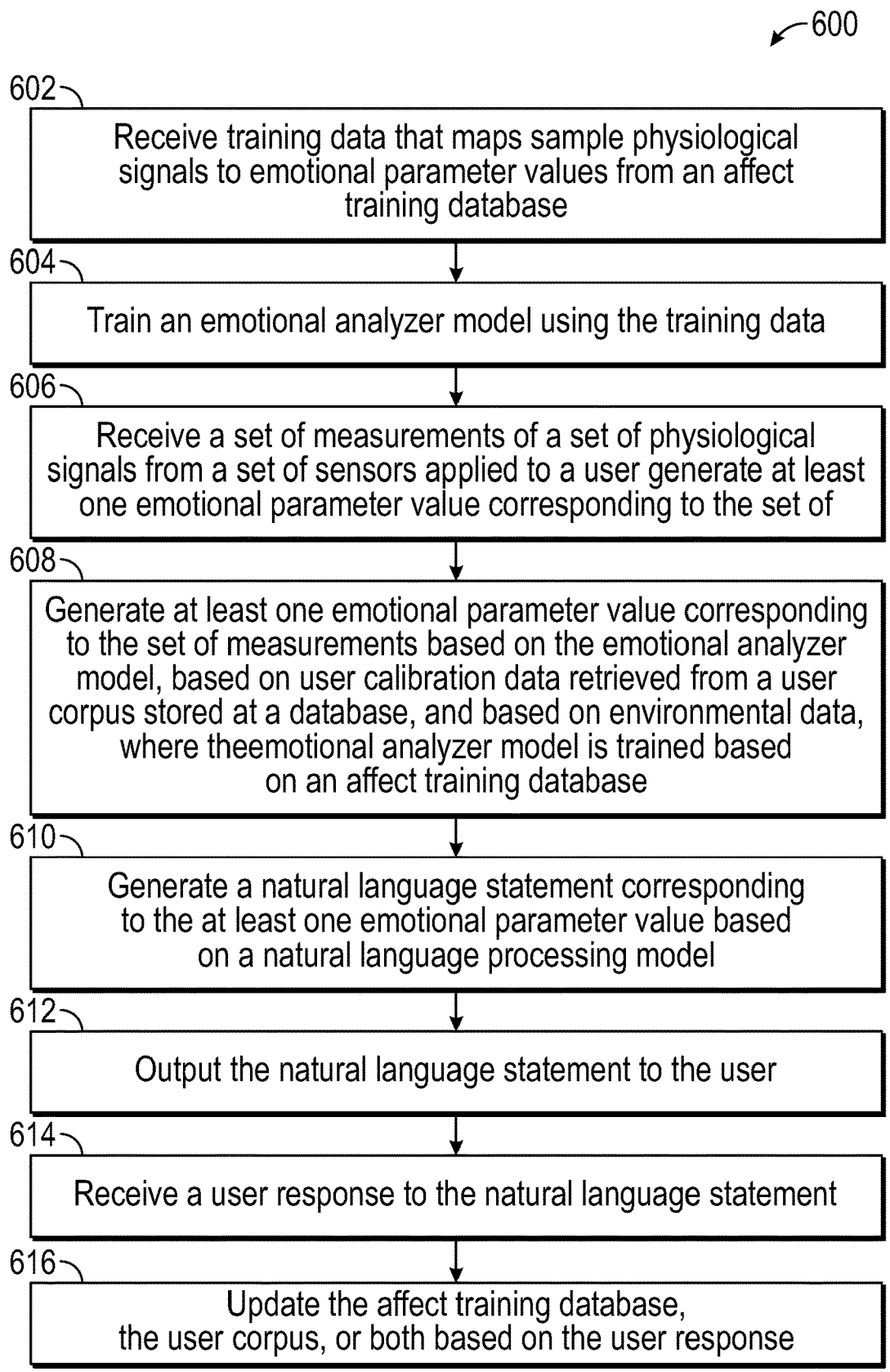
FIG. 6 is a flow diagram depicting an example of a method for training an emotional analyzer model and for providing user support in a robotic-assisted user environment.

Referring to FIG. 6, an example of a method 600 for providing user support in a robotic-assisted user environment is depicted. The method 600 may include receiving training data that maps sample physiological signals to emotional parameter values from an affect training database, at 602. For example, the processor 102, or another processing device used for training, may receive the training data 192 that maps the sample physiological signals 302-304 to the emotional parameter values 306 from the affect training database 190.

The method 600 may further include training an emotional analyzer model using the training data, at 604. For example, the emotional analyzer model 140 may be trained using the training data 192.

The method 600 may also include receiving a set of measurements of a set of physiological signals from a set of sensors applied to a user, at 606. For example, the set of measurements 132 of the set of physiological signals 122 may be received by the processor 102 from the set of sensors 110, which may be applied to the user 120.

The method 600 may include generating at least one emotional parameter value corresponding to the set of measurements based on an emotional analyzer model, based on user calibration data retrieved from a user corpus stored at a database, and based on environmental data, where the emotional analyzer model is trained based on the affect training database, at 608. For example, the at least one emotional parameter value 142 may be generated and may correspond to the set of measurements 132. The emotional parameter value 142 may be generated based on the emotional analyzer model 140, based on the user calibration data 184, and based on the environmental data 174.

The method 600 may further include generating a natural language statement corresponding to the at least one emotional parameter value based on a natural language processing model, at 610. For example, the natural language statement 152 may be generated based on the natural language processing model 150.

The method 600 may also include outputting the natural language statement to the user, at 612. For example, the natural language statement 152 may be output to the user 120.

The method 600 may include receiving a user response to the natural language statement, at 614. For example, the user response 124 may be received by the processor 102.

The method 600 may further include updating the affect training database, the user corpus, or both based on the user response, at 616. For example, the affect training database 190, the user corpus 182, or both may be updated based on the user response 124.

A benefit of the method 600 is that a robotic co-pilot can respond to a user in an emotionally intelligent manner, both in actions and communications. This may enable a user and the robotic co-pilot to work more effectively together.

Figure 7:
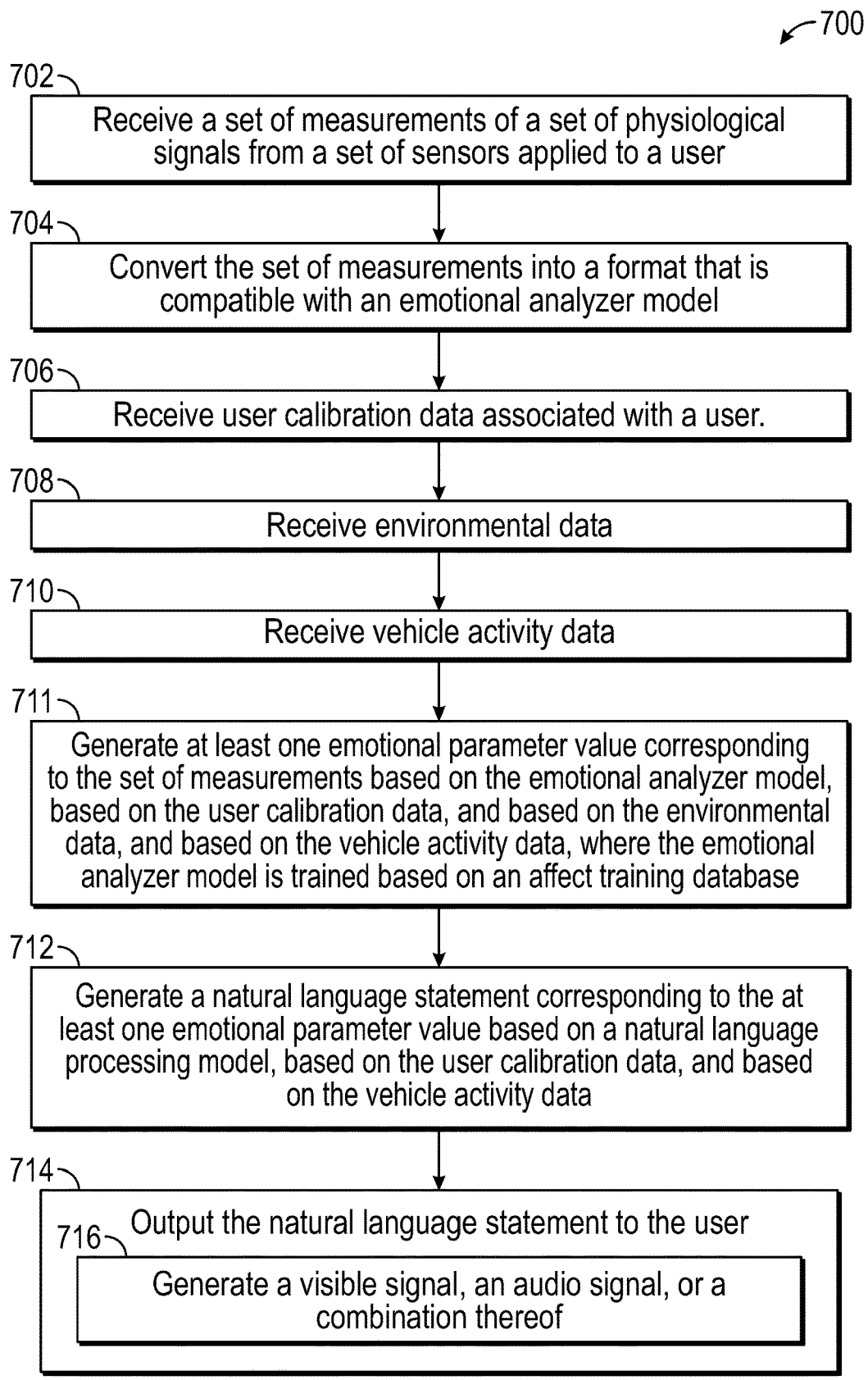
FIG. 7 is a flow diagram depicting an example of a method for providing user support in a robotic-assisted user environment.

Referring to FIG. 7, an example of a method 700 for providing user support in a robotic-assisted user environment is depicted and may correspond to portions (i.e., 606-612) of the method 600 with some additional elements. For example, the method 700 may include receiving a set of measurements of a set of physiological signals from a set of sensors applied to a user, at 702. For example, the set of measurements 132 of the set of physiological signals 122 may be received by the processor 102 from the set of sensors 110, which may be applied to the user 120.

The method 700 may further include converting the set of measurements into a format that is compatible with an emotional analyzer model, at 704. For example, the measurements 132 may be converted into the compatible measurements 134.

The method 700 may also include receiving user calibration data associated with a user, at 706. For example, the user calibration data 184 may be received.

The method 700 may include receiving environmental data, at 708. For example, the environmental data 174 may be received.

The method 700 may further include receiving vehicle activity data, at 710. For example, the vehicle activity data 172 may be received.

The method 700 may also include generating at least one emotional parameter value corresponding to the set of measurements based on an emotional analyzer model, based on the user calibration data, based on the environmental data, and based on the vehicle activity data, where the emotional analyzer model is trained based on an affect training database, at 711. For example, the at least one emotional parameter value 142 may be generated.

The method 700 may further include generating a natural language statement corresponding to the at least one emotional parameter value based on a natural language processing model, based on the user calibration data, and based on the vehicle activity data, at 712. For example, the natural language statement 152 may be generated.

The method 700 may also include outputting the natural language statement to the user, at 714. For example, the natural language statement 152 may be output to the user 120. Outputting the natural language statement may include generating a visible signal, an audio signal, or a combination thereof, at 716. For example, the visual signal 162, the audio signal 164, or both may be generated.

A benefit of the method 700 is that a robotic co-pilot can respond to a user in an emotionally intelligent manner, both in actions and communications, and the interaction may be fine tuned based on user calibration data, environmental data, and vehicle activity data. This may enable a user and the robotic co-pilot to work more effectively together.

Although various examples have been shown and described, the present disclosure is not so limited and will be understood to include all such modifications and variations as would be apparent to one skilled in the art.

What is claimed is:

1. A system for providing user support in a robotic-assisted user environment, the system comprising:
    at least one processor; and
    memory storing instructions that, when executed by the at least one processor, cause the at least one processor to:
    receive a set of measurements of a set of physiological signals from a set of sensors applied to a user;
    generate one or more emotional parameter values corresponding to the set of measurements based on an emotional analyzer model, wherein the one or more emotional parameter values include a valence parameter, an arousal parameter, a dominance parameter, an emotion parameter, and a strength parameter; and
    generate a natural language statement corresponding to the one or more emotional parameter values based on a natural language processing model, wherein the natural language statement indicates that control will be taken of one or more vehicle systems usable to operate an aircraft; and
    control the one or more vehicle systems.

2. The system of claim 1, wherein the set of sensors includes one or more microphones, one or more biometric sensors, one or more cameras, or any combination thereof.

3. The system of claim 1, wherein the set of physiological signals includes a galvanic skin response, a blood volume measurement, a heart rate variability, an electroencephalogram, an eye dilation measurement, a thermal response, a muscle response, or any combination thereof.

4. The system of claim 1, wherein the instructions further cause the at least one processor to:
    convert the set of measurements into a format that is compatible with the emotional analyzer model.

5. The system of claim 1, wherein the instructions further cause the at least one processor to:
    receive user calibration data associated with the user, wherein the one or more emotional parameter values is generated based at least in part on the user calibration data, and wherein the natural language statement is generated based at least in part on the user calibration data.

6. The system of claim 5, wherein the user calibration data includes a value representing a level of emotional response associated with a user, a communication preference value, or both.

7. The system of claim 5, further comprising:
    a user corpus stored in a database, the user corpus including the user calibration data associated with the user along with additional user calibration data associated with additional users, wherein the user calibration data is retrieved from the user corpus.

8. The system of claim 1, wherein the instructions further cause the at least one processor to:
    receive environmental data, wherein the one or more emotional parameter values are generated based at least in part on the environmental data.

9. The system of claim 8, wherein the environmental data indicates a temperature, a pressure, weather conditions, visual conditions, or any combination thereof.

10. The system of claim 1, wherein the instructions further cause the at least one processor to:
    receive vehicle activity data, wherein the one or more emotional parameter values are generated based at least in part on the vehicle activity data, and wherein the natural language statement is generated based at least in part on the vehicle activity data.

11. The system of claim 10, wherein the vehicle activity data indicates a phase of flight associated with the aircraft, activated warnings associated with the aircraft, air traffic control communications, aircraft imaging or radar inputs, or any combination thereof.

12. The system of claim 1, further comprising:
    an affect training database storing training data that maps sample physiological signals to emotional parameter values, wherein the emotional analyzer model is a machine learning model trained using the training data.

13. The system of claim 1, wherein the instructions further cause the at least one processor to:
    output the natural language statement to the user;
    receive a user response to the natural language statement; and
    initiate an update to an affect training database, a user corpus database, or both based on the user response.

14. The system of claim 1, implemented within a robotic-assisted transport vehicle or a vehicle control system.

15. A method for providing user support in a robotic-assisted user environment, the method comprising:
    receiving a set of measurements of a set of physiological signals from a set of sensors applied to a user;
    generating a set of emotional parameter values corresponding to the set of measurements based on an emotional analyzer model, based on user calibration data retrieved from a user corpus stored at a database, and based on environmental data, wherein the emotional analyzer model is trained based on an affect training database, and wherein the set of emotional parameter values includes each of a valence parameter value, an arousal parameter value, a dominance parameter value, an emotion parameter value, and a strength parameter value;
    generating a natural language statement corresponding to the set of emotional parameter values based on a natural language processing model;
    outputting the natural language statement to the user;
    receiving a user response to the natural language statement; and
    updating the affect training database, the user corpus, or both based on the user response.

16. The method of claim 15, further comprising:
    receiving training data that maps sample physiological signals to emotional parameter values from the affect training database; and training the emotional analyzer model using the training data.

17. The method of claim 15, wherein outputting the natural language statement to the user includes generating a visible signal, and audio signal, or a combination thereof.

18. A system for providing pilot or controller support in a reduced crew transport environment, the system comprising:

a set of sensors configured to collect a set of measurements of a set of physiological signals of a pilot;

an emotional analyzer model usable to generate at least one emotional parameter value corresponding to the set of measurements, wherein the one or more emotional parameter values include a valence parameter, an arousal parameter, a dominance parameter, an emotion parameter, and a strength parameter; and a natural language processing model usable to generate a natural language statement corresponding to the at least one emotional parameter value for output to the pilot, wherein the natural language statement indicates that control will be taken of one or more aircraft systems usable to operate an aircraft, and wherein the system takes control of the one or more aircraft systems from the pilot.

19. The system of claim 18, wherein the one or more aircraft systems provide environmental data and aircraft activity data for use in generating the at least one emotional parameter value, and wherein the system further comprises:

an affect training database to provide training data for training the emotional analyzer model; and a user corpus stored in a database, the user corpus including user calibration data associated with the pilot to provide pilot-specific data for use in generating the at least one emotional parameter value and for use in generating the natural language statement.

20. The system of claim 18, wherein the set of sensors includes one or more microphones, one or more biometric sensors, one or more cameras, or any combination thereof.

* * * * *